United States Patent [19]

Igich

[11] 4,119,101
[45] Oct. 10, 1978

[54] MULTIPLE LUMEN ENDOTRACHEAL TUBE AND CUFF WITH LIMITED INFLATION AND PRESSURE

[76] Inventor: Victor Igich, 2022 44th Ave., Gulfport, Miss. 39501

[21] Appl. No.: 662,394

[22] Filed: Mar. 1, 1976

[51] Int. Cl.² .............................................. A61M 25/00
[52] U.S. Cl. .................................................... 128/351
[58] Field of Search ............ 128/351, 349 B, 349 BV, 128/350 R, 348, 188, 145.8, 145.6, 145.5, 184

[56] References Cited

U.S. PATENT DOCUMENTS

| | | | |
|---|---|---|---|
| 2,582,210 | 1/1952 | Stanton | 128/188 X |
| 3,158,152 | 11/1964 | Bloom | 128/145.5 |
| 3,297,027 | 1/1967 | Rusch | 128/351 X |
| 3,504,676 | 4/1970 | Lomholt | 128/351 |
| 3,848,605 | 11/1974 | Harautuneian et al. | 128/351 |
| 3,905,361 | 9/1975 | Hewson et al. | 128/351 X |

Primary Examiner—Robert W. Michell
Assistant Examiner—Michael H. Thaler
Attorney, Agent, or Firm—James B. Lake, Jr.

[57] ABSTRACT

An inflatable cuff of an endotracheal tube, having multiple lumens, is connected through a lumen to an exterior collapsible container; the cuff, lumen and collapsible container defining a closed pneumatic system that is adapted to receive a metered amount of gas sufficient to inflate the cuff, when the collapsible container is fully collapsed, to seal at a pressure, responsive to said metered amount of gas, undamaging to a trachea in which the tube is inserted. A relatively rigid and larger container encloses the collapsible container and is connected together with another lumen to a common source of air at lung inflation pressure in normal breathing pulsations whereby the trachea is invariably sealed at undamaging pressure unaffected by the amount of, and variation in, the lung inflation pressure of the supplied air, the sealing being in synchronization with lung inflation by the normal breathing pulsations. The remaining lumens may be used jointly and severally to remove fluids from and introduce medicines in the lungs.

3 Claims, 3 Drawing Figures

MULTIPLE LUMEN ENDOTRACHEAL TUBE AND CUFF WITH LIMITED INFLATION AND PRESSURE

BACKGROUND OF THE INVENTION

1. Field of the Invention

The invention relates generally to cuffed endotracheal tubes, and more particularly to a multi-lumen endotracheal tube with closed cuff inflation system that positively limits cuff inflation and resultant tracheal sealing pressure.

2. Description of the Prior Art

The prior art teaches a closed hydraulic cuff inflation system operable by a non-pulsating gravity head that maintains a constant cuff inflation and which runs into trouble with air locks and fluid leaks. See Jackson US Pat. Nos. 3,766,927 and 3,854,484. The rest of the prior art teach cuff inflation by direct connection with an inflation source, a malfunction of which can cause an over inflation damaging to a trachea. See Balzell US Pat. Nos. 3,884,242; Hayward 3,709,227; Goodyear 3,731,692; McGinnis 3,642,005; Puig 3,481,339; Sheridan et al 3,625,793; and Baran 3,173,418.

SUMMARY OF THE INVENTION

It is an object of the invention to provide an endotracheal tube with an inflatable cuff that cannot be overinflated in operation.

Another object of the invention is to provide a multilumen endotracheal tube for use with said inflatable cuff.

DETAILED DESCRIPTION OF THE INVENTION

Figures 1, 2, 3:
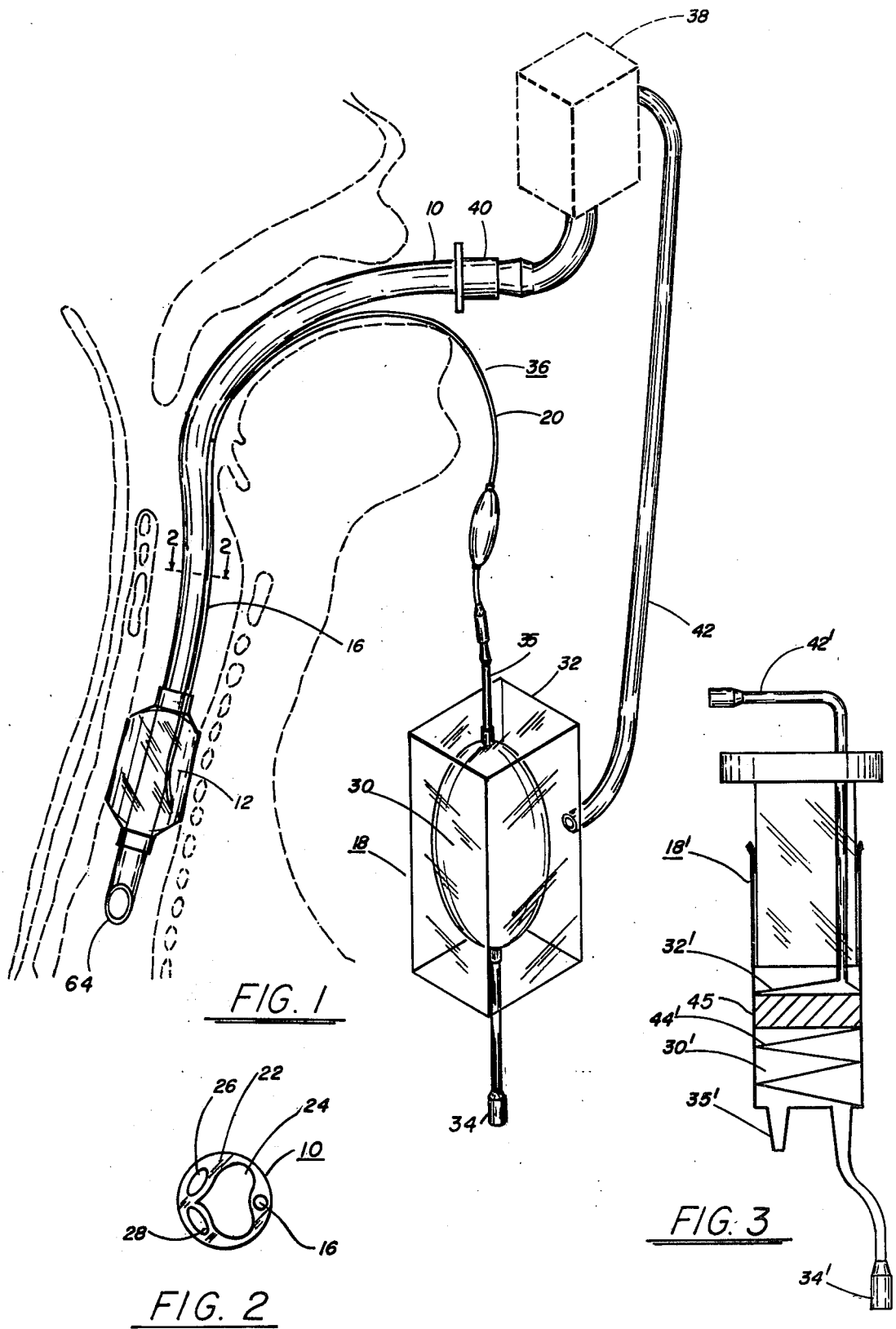
FIG. 1 is a side elevation of the invention in operable positon.
FIG. 2 is a cross-sectional view of a multi-lumen endotracheal tube.
FIG. 3 is a second specie of a portion of FIG. 1.

Referring to FIGS. 1 and 2, the invention comprises a multiple-lumen endotracheal tube 10, an inflatable cuff 12 mounted around said tube adjacent its distal end 14 and inflatable through one lumen 16 of its multiple lumens, and a pressure transfer device 18 connected through a small tube 20 to lumen 16 and cuff 12.

Endotracheal tube 10 comprises a plastic tube of conventional exterior appearance, but having longitudinal walls 22 extending interiorly the length of tube 10 dividing it into a large lumen 24 and two smaller lumens 26 and 28, all of which can be used jointly and severally for the inflation of lungs, the removal of liquid therefrom, and the supply of medication thereto.

Cuff 12 is inflatable for sealing a trachea in which endtracheal tube 10 is inserted. The sealing pressure is a direct function of the amount of inflation, and it is most important that said pressure be kept to a minimum for sealing to prevent necrosis of engaged areas of the trachea.

Pressure transfer device 18 comprises in its preferred embodiment a collapsible container 30 mounted in a relatively rigid outer container 32. A syringe puncture plug 34 outside and below outer container 32 connects with collapsible container 30 for inflating it with a metered amount of gas. A connector 35 mounted outside and above outer container 32 and extending inside connects collapsible container 30 to free end of small tube 20; container 30, small tube 20, lumen 16 and cuff 12 forming a closed pneumatic system 36. Outer container 32 is connected to a supply of air at lung inflation pressure in normal breathing pulsations such as the output of well known respirators and indicated by a block 38 in FIG. 1 which is also connected to the proximal end 40 and at least large lumen 24 of endotracheal tube 10.

In use, the closed pneumatic system 36 is exhausted by means of a syringe (not shown) the needle of which is inserted in puncture plug 34. By the same means a metered amount of gas is injected in system 36 sufficient to inflate cuff 12 to minimum sealing pressure when collapsible container 30 is collapsed fully. This is accomplished by the pulsating air pressure from lung inflation supply 38 being introduced into outer container 32. The same supply goes to at least lumen 24 of tube 10 to inflate the lungs as the trachea is sealed by cuff 12. As each pulsation ends in the breathing rythm, the air in the lungs at inflation pressure deflates cuff 12 and escapes to lower atmospheric outside pressure. The gas in cuff 12 escapes through lumen 16, small tube 20 into collapsible container 30 which has a greater volume than cuff 12 and offers no resistance to the gas. To be sure the cuff is fully deflated for best exhalation, the collapsible container 30 can be made of material having the ability to return to an uncollapsed state at the end of each pressure pulsation to outer container 32. Tube 42 connects container 30 with respirator 38.

Thus it can be seen that whatever the lung inflation air pressure may be or may be varied, the cuff sealing inflation and pressure remain at the optimum established by the amount of the gas injected into the closed pneumatic system.

A second specie of pressure transfer device 18 is shown in FIG. 3, with corresponding parts that function similarly numbered similarly and with primes. The property of collapsible container 30 to return to its original form is provided in the second specie by a spring 44 and plunger 45.

What is claimed is:

1. An endotracheal tube, with an inflatable cuff for pressure sealing and unsealing a trachea, mounted around said endotracheal tube for use with a respirator providing pulsating pressure output in artificial respiration, comprising:

(a) multiple lumen means, having oppositely disposed ends, running the length of said endotracheal tube which is adapted for one end of said oppositely disposed ends to connect with said respirator, and the other end of said oppositely disposed ends to be inserted in a trachea for aspirating lungs and an additional lumen means, having oppositely disposed free ends respectively terminating exteriorly adjacent said respirator and interiorly in said inflatable cuff; and (b) a pressure transfer device means located outside of said endotracheal tube and having a relatively rigid outer container means adjusted to be connected to said respirator in parallel with said endotracheal tube for receiving a part of said pulsating pressure output of said respirator, and a collapsible container, that is deflatable and self-inflatable, mounted in said outer container means and connected to said additional lumen means by its exteriorly terminating oppositely disposed end for defining with said inflatable cuff a closed pneumatic system in which a limited amount of gas is injectable therein that is responsive to said part of the pulsating pressure output of the respirator received in said outer container to alternately collapse said collapsible container and inflate said inflatable cuff, and vice versa, said rigid outer container being closed except for its connection to the respirator, said collapsible container being closed except for its connection to said additional lumen means.

2. Pressure transfer device means as described in claim 1 wherein said relatively rigid outside container comprise:
 (a) a container that is flexible at pressures greater than pressures necessary to collapse said collapsible container.

3. An endotracheal tube, with an inflatable cuff for pressure sealing and unsealing a trachea, mounted around said endotracheal tube for use with a respirator providing pulsating pressure output in artificial respiration comprising:
 (a) multiple lumen means, having oppositely disposed ends, running the length of said endotracheal tube which is adapted for one end of said oppositely disposed ends to connect with said respirator, and the other end of said oppositely disposed ends to be inserted in a trachea for aspirating lungs and an additional lumen means, having oppositely disposed free ends respectively terminating exteriously adjacent said respirator and interiorly in said inflatable cuff and
 (b) a pressure transfer device means located outside of said endotracheal tube and having a relatively rigid container means adapted to be connected to said respirator in parallel with said endotracheal tube for receiving a part of said pulsating pressure output of said respirator, said pressure transfer device means being
 a cylinder having oppositely disposed ends, with a plunger, having oppositely dsposed sides slidably mounted in said cylinder to define on one side of said plunger relatively rigid container, and on the other side of said plunger a collapsing container said collapsible container being connected to said additional lumen means by its exteriorly terminating oppositely disposed end for defining within said inflatable cuff a closed pneumatic system in which a limited amount of gas in injectable therein that is responsive to said part of the pulsating pressure output of the respirator received in said rigid container to alternately collapse said collapsible container and inflate said inflatable cuff and vice versa
 a spring mounted in said collapsing container and engaging said plunger to return to its original position, thereby helping deflate said inflatable cuff and return said limited amount of gas to said collapsible container.

* * * * *